US007025730B2

(12) United States Patent
Cho et al.

(10) Patent No.: US 7,025,730 B2
(45) Date of Patent: Apr. 11, 2006

(54) SYSTEM AND METHOD FOR AUTOMATICALLY MONITORING AND DELIVERING THERAPY FOR SLEEP-RELATED DISORDERED BREATHING

(75) Inventors: Yong K. Cho, Maple Grove, MN (US); Mark K. Erickson, Brooklyn Park, MN (US); H. Toby Markowitz, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 46 days.

(21) Appl. No.: 10/419,465

(22) Filed: Apr. 21, 2003

(65) Prior Publication Data

US 2004/0138719 A1    Jul. 15, 2004

Related U.S. Application Data

(60) Provisional application No. 60/439,184, filed on Jan. 10, 2003.

(51) Int. Cl.
*A61B 5/08* (2006.01)

(52) U.S. Cl. ......................... 600/529; 607/42

(58) Field of Classification Search ........... 128/200.24, 128/204.18–204.19, 204.21, 204.29, 205.13–18; 600/529–543; 607/2, 3, 5–9, 17–56, 30, 607/32, 42, 118
See application file for complete search history.

(56) References Cited

U.S. PATENT DOCUMENTS

| 4,289,142 A | 9/1981 | Kearns |
| 5,117,824 A | 6/1992 | Keimel et al. |
| 5,146,918 A | 9/1992 | Kallok et al. |
| 5,174,287 A | 12/1992 | Kallok et al. |
| 5,199,424 A * | 4/1993 | Sullivan et al. ......... 128/204.18 |
| 5,215,082 A | 6/1993 | Kallok et al. |
| 5,245,995 A | 9/1993 | Sullivan et al. |
| 5,335,657 A * | 8/1994 | Terry et al. .................... 607/45 |
| 5,353,788 A | 10/1994 | Miles |
| 5,540,733 A | 7/1996 | Testerman et al. |
| 5,549,655 A * | 8/1996 | Erickson ....................... 607/42 |
| 5,551,419 A | 9/1996 | Froehlich et al. |
| 5,630,834 A | 5/1997 | Bardy |
| 5,645,053 A | 7/1997 | Remmers et al. |
| 5,814,087 A | 9/1998 | Renirie |
| 5,987,352 A | 11/1999 | Klein et al. |

(Continued)

FOREIGN PATENT DOCUMENTS

EP    0 702 979 A2    3/1996

(Continued)

*Primary Examiner*—Robert L. Nasser
*Assistant Examiner*—Patricia Mallari
(74) *Attorney, Agent, or Firm*—Daniel G. Chapik; Girma Walde-Michael

(57) ABSTRACT

The invention relates generally to a system and method for monitoring and automatically delivering a therapy for sleep-related disordered breathing. In one form the present invention relates to an external device for monitoring for sleep-related disordered breathing in communication with an implantable medical device for delivering an electrical stimulation therapy. In another form the present invention relates to an implantable medical device for detecting sleep-related disordered breathing episode(s) and an external apparatus (e.g., a CPAP machine) for providing therapy to terminate, and/or reduce, said episode(s). In this form of the invention, the implantable medical device communicates with the external apparatus so that the therapy provided corresponds in magnitude and duration to the severity and/or length of the episode(s). In yet another form, an implantable apparatus detects said disordered breathing episode(s) and a hybrid therapy is provided by both the implantable apparatus and an external apparatus.

12 Claims, 8 Drawing Sheets

U.S. PATENT DOCUMENTS

| | | | |
|---|---|---|---|
| 6,047,203 A | 4/2000 | Sackner et al. | |
| 6,070,101 A | 5/2000 | Struble et al. | |
| 6,126,611 A | 10/2000 | Bourgeois et al. | |
| 6,132,384 A * | 10/2000 | Christopherson et al. | 600/529 |
| 6,251,126 B1 * | 6/2001 | Ottenhoff et al. | 607/42 |
| 6,269,269 B1 | 7/2001 | Ottenhoff et al. | |
| 6,398,739 B1 | 6/2002 | Sullivan et al. | |
| 6,415,183 B1 * | 7/2002 | Scheiner et al. | 607/42 |
| 6,480,742 B1 | 11/2002 | Stahmann et al. | |
| 6,641,542 B1 * | 11/2003 | Cho et al. | 600/529 |
| 6,651,652 B1 * | 11/2003 | W.ang.rd | 128/200.24 |
| 2002/0193697 A1 | 12/2002 | Cho et al. | 600/529 |
| 2004/0088027 A1 * | 5/2004 | Burnes et al. | 607/60 |

FOREIGN PATENT DOCUMENTS

EP      0 940 155 A2      9/1999

* cited by examiner

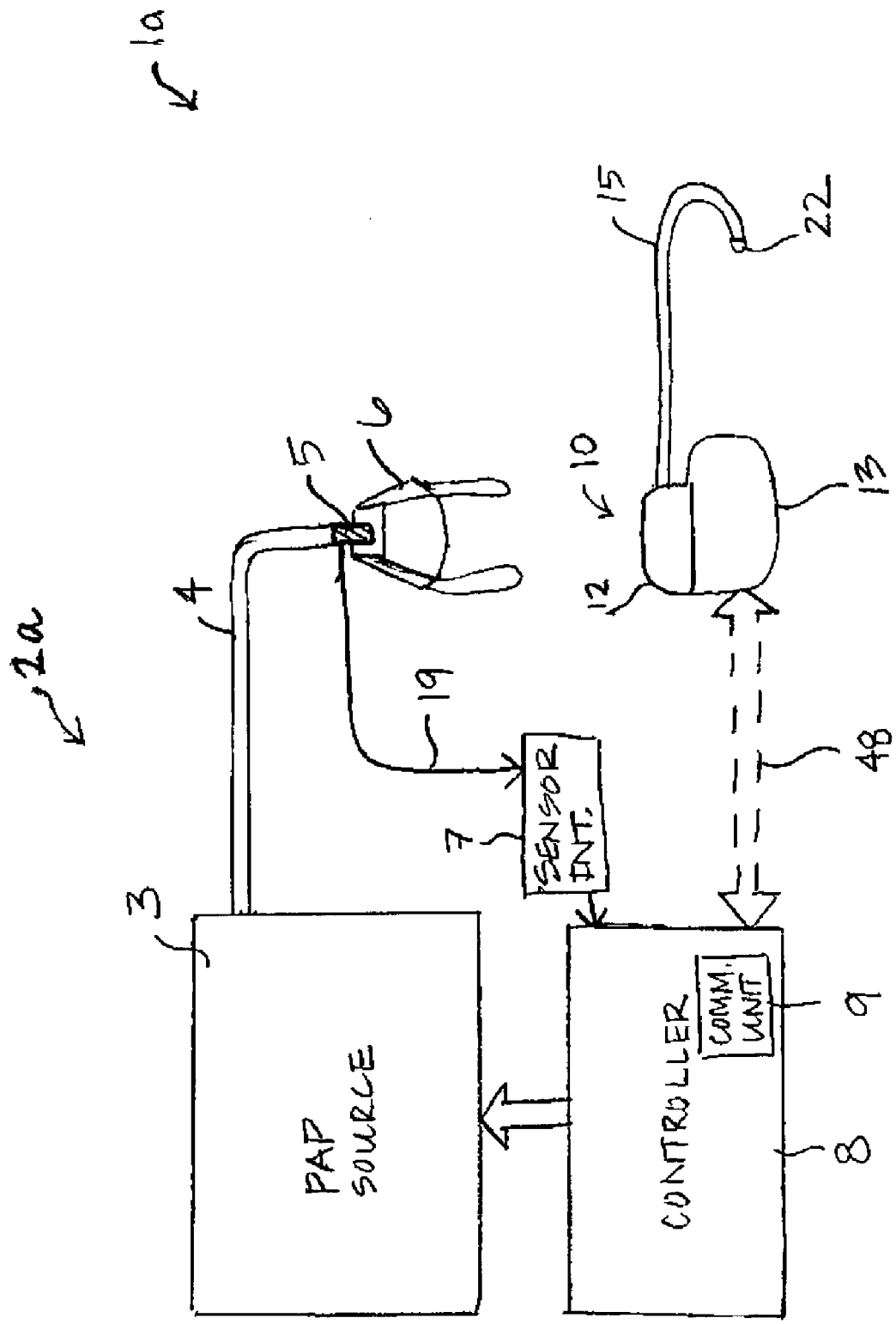

SYSTEM AND METHOD FOR AUTOMATICALLY MONITORING AND DELIVERING THERAPY FOR SLEEP-RELATED DISORDERED BREATHING

CROSS REFERENCE TO RELATED APPLICATION

This patent disclosure claims the benefit of the filing of provisional U.S. patent application Ser. No. 60/439,184 filed 10 Jan. 2003.

FIELD OF THE INVENTION

The present invention relates generally to a system and method for monitoring and automatically delivering a therapy for sleep-related disordered breathing. More particularly, the present invention relates to an external device for monitoring for sleep-related disordered breathing in communication with an implantable medical device for delivering an electrical stimulation therapy.

BACKGROUND OF THE INVENTION

Sleep-related breathing disorders include sleep apnea and nocturnal Cheyne-Stokes breathing. Cheyne-Stokes breathing is the waxing and waning of respiration associated with congestive heart failure. Sleep apnea, the temporary cessation of respiratory airflow during sleep, is generally considered a medical syndrome that occurs in at least three recognized forms. The first is central sleep apnea, associated with the failure of the central nervous system to automatically initiate and control respiration. The second is obstructive sleep apnea, associated with an obstruction of the airways due to their collapse. A third, mixed form is the combination of a central nervous system failure to drive ventilatory effort and obstructive apnea. The consequences of sleep-disordered breathing, daytime sleepiness and associated cardiovascular diseases, significantly impair patient lifestyle and increase morbidity risk. Various approaches have been taken to detect and treat sleep-related disordered breathing.

A standard diagnostic approach for sleep apnea includes polysomnography, which requires the patient to stay overnight in a hospital for observation. Polysomnography involves monitoring of multiple parameters including electroencephalography, electromyography, electrocardiography, oximetry, airflow, respiratory effort, snoring, body position and blood pressure. This intensive and costly approach is not practical for screening large numbers of patients, yet the prevalence of undiagnosed sleep apnea in the U.S. is thought to be in the millions with on the order of 2% of middle-aged women and 4% of middle-aged men having sleep apnea syndrome. See Young T. et al., "The occurrence of sleep-disordered breathing among middle-aged adults," *New England J. Med.* 1993;328:1230–1235. An apnea-hypopnea index (AHI) is used by physicians to gauge the severity of sleep apnea. AHI is the number of apnea-hypopnea episodes occurring per hour during a monitored period. It is estimated that 9% of women and 24% of men have an AHI greater than 5, indicating at least a mild to moderate sleep apnea condition.

Sleep apnea is known to have cardiovascular consequences including changes in cardiac rhythm, hemodynamic fluctuations, and hypertension. Sleep-related breathing disorders are associated with an increase in sympathetic nerve activity leading to an increase in blood pressure. The increased blood pressure increases carotid baroreceptor activity which decreases the baroreceptor reflex which in turn reduces the respiration rate and perhaps pharyngeal muscle tone and an overall worsening sleep apnea condition. In patients with sleep apnea syndrome, atrial overdrive pacing significantly reduces the number of episodes of central or obstructive sleep apnea. See Garrigue S, et al., N Engl J Med 2002;346:404–412. Low oxygen levels due to sleep apnea are associated with an increased morbidity due to cardiovascular complications, including heart attack and stroke. Sleep apnea is largely undiagnosed in heart failure patients but significantly worsen a patient's prognosis.

A method for screening and diagnosing sleep-related disordered breathing that is less costly and less stressful to the patient than polysomnography is needed, therefore, in order to reach the large number of patients having undiagnosed sleep apnea. Once diagnosed, a common mode of treatment is the application of continuous positive airway pressure (CPAP) to maintain patency of the airways. The applied pressure is generally prescribed by a sleep disorder specialist, typically requiring a second overnight polysomnographic study. CPAP applied throughout the night can cause considerable stress to the patient because the actual pressure required to maintain airway patency can vary throughout the night or from night-to-night due to body position, sleep state, or other factors. Application of continuous pressure throughout the night can therefore lead to patient discomfort, resulting in poor patient compliance.

Considerable development effort has been made to provide positive airway pressure systems that sense the patient's airway pressures or other respiratory parameters and automatically provide positive pressure in response to the sensed parameters. Positive airway pressure is then applied only as needed and/or at the minimum pressure needed to maintain airway patency. This treatment optimization reduces patient discomfort and lessens the likelihood of undesired arousals due to CPAP delivery. Apparatus and methods for controlling positive-airway pressure are generally disclosed in U.S. Pat. No. 5,645,053 issued to Remmers et al., U.S. Pat. No. 5,245,995 issued to Sullivan et al., U.S. Pat. No. 5,353,788 issued to Miles et al., U.S. Pat. No. 5,551,419 issued to Froehlich et al., and U.S. Pat. No. 6,398,739 issued to Sullivan et al., all of which patents are incorporated herein by reference in their entirety.

Alternative therapeutic approaches toward treating sleep-related breathing disorders involve detecting the onset of an apnea episode and then delivering electrical stimulation therapy to either maintain airway patency or counteract autonomic-mediated causes of apnea. For example, electrical stimulation of the hypoglossal nerve, muscles of the upper airways, vagus nerve or overdrive cardiac pacing have all been proposed or attempted clinically. Reference is made to U.S. Pat. No. 5,540,733 issued to Testerman et al., U.S. Pat. No. 5,174,287 issued to Kallok, U.S. Pat. No. 6,251,126 issued to Ottenhoff et al., U.S. Pat. No. 5,335,657 issued to Terry, Jr., et al., and U.S. Pat. No. 6,126,611 issued to Bourgeois et al., all of which patents are incorporated herein by reference in their entirety.

Detection of sleep apnea for the purposes of triggering the delivery of a sleep apnea therapy may be based on respiratory monitoring. Measuring respiratory effort by monitoring airway pressures is generally disclosed in the above-cited U.S. Pat. No. 5,540,733 issued to Testerman and in U.S. Pat. No. 6,132,384 issued to Christopherson et al. A method for monitoring electrical activity associated with contractions of the diaphragm and the pressure within the thorax and upper airway is generally disclosed in U.S. Pat. No. 5,174,287 issued to Kallok.

One limitation of apnea detection methods which require the use of implanted sensors relates to the normal complications which can occur with implanted devices, such as infection or dislodgement. Non-invasive sensing of respiration for apnea detection using a breathing mask poses no substantial risk to the patient but is limited by patient compliance. A breathing mask used for sensing respiration and delivering positive airway pressure, however, may be poorly tolerated by a patient due primarily to the discomfort and stress caused by the application of positive pressure and the required air hose which can encumber patient movement and position during the night.

A therapy for treating sleep apnea should be aimed at reducing or eliminating episodes of sleep disordered breathing without causing patient arousals or discomfort. Any intervention which causes fragmentation of a patient's sleep will ultimately result in excessive daytime sleepiness and not meet the therapeutic objectives for improving patients' sleep. An improved system and method for automatically monitoring and delivering a therapy for sleep-related disordered breathing are needed to improve patient compliance and acceptance by providing an effective therapy that does not arouse the patient or cause discomfort or stress that leads to patient incompliance.

SUMMARY OF THE INVENTION

An improved system and method for treating sleep-related disordered breathing (SRDB) is provided by the present invention. The system includes an external monitoring system for detecting SRDB and an implantable medical device for delivering a SRDB therapy. The external monitoring system is used for screening for and diagnosing SRDB and preferably includes a breathing mask equipped with sensors for monitoring patient respiration. The external system further includes a control unit for receiving and processing sensor input for detecting apnea or hypopnea. The control unit may further determine metrics of SRDB based on detected apnea/hypopnea events. The external system may optionally include a positive airway pressure source coupled to the breathing mask via an air hose for automatically delivering positive pressure to maintain airway patency when apnea is detected. Alternatively, the external system is provided for monitoring purposes only, eliminating the need for an airhose attached to the breathing mask and allowing the patient freer movement during the night.

Detection of SRDB and SRDB metrics determined by the external system are used for setting and/or controlling SRDB therapy delivered by the implantable medical device (IMD). SRDB metrics may be reviewed by a physician for manual selection of IMD therapy parameters. In a preferred embodiment, the external system is in telemetric communication with the IMD such that apnea detection, SRDB metrics, or a change in SRDB metrics that requires a change in therapy delivery may be communicated to the IMD.

The IMD is preferably a device capable of delivering electrical stimulation therapy. In a preferred embodiment, the IMD is a cardiac pacemaker capable of delivering nocturnal overdrive pacing. In alternative embodiments, the IMD may deliver electrical stimulation to the upper airway muscles, the hypoglossal nerve, the vagus nerve, or other excitable tissue for the treatment of sleep apnea. Operational parameters controlling the delivery of electrical impulses are preferably optimized based on monitored SRDB metrics determined by the external device. A closed-loop system allows SRDB metrics to be re-determined continuously or periodically such that a worsening in SRDB may be responded to by adjusting IMD therapy delivery. A closed-loop system additionally or alternatively allows IMD therapy to be delivered in an episode-based mode. Upon apnea detection or prediction, a therapy trigger signal may be transmitted to the IMD from the external device such that therapy is delivered only as needed.

BRIEF DESCRIPTION OF THE DRAWINGS

FIG. 1A is a schematic diagram of a system provided by the present invention for monitoring for sleep-related disordered breathing and delivering a therapeutic intervention.

DETAILED DESCRIPTION OF THE INVENTION

Figure 1B:
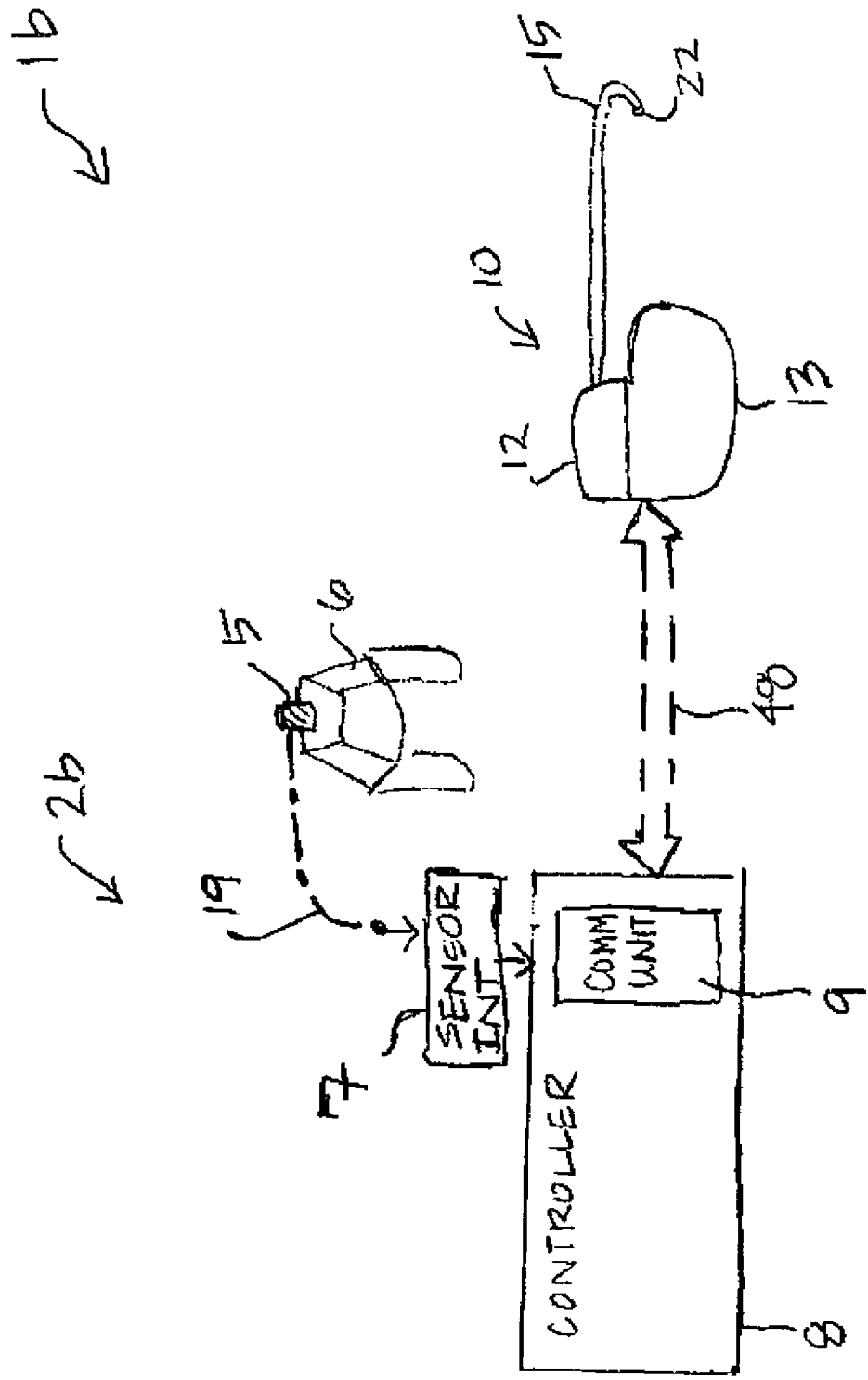
FIG. 1B is a schematic diagram of an alternative embodiment of a system provided by the present invention for monitoring for sleep-related disordered breathing and delivering a therapeutic intervention.

FIG. 1A is a schematic diagram of a system provided by the present invention for monitoring for sleep-related disordered breathing and delivering a therapeutic intervention. The system, generally labeled as 1A, includes an external monitoring system 2A for monitoring respiration and an implantable medical device 10 for delivering a therapy for alleviating SRDB. The external monitoring system 2A, in this embodiment, is capable of delivering positive airway pressure for maintaining airway patency and is therefore referred to herein as an "automatic CPAP system". Accordingly, external system 2A includes a positive airway source 3 connected to a patient mask 6 via an air hose 4. Sensor interface 7 receives input on signal line 19 from sensors 5 located in mask 6, or alternatively within air hose 4, and provides output to controller 8. Controller 8 is preferably a microprocessor based system, which may be a personal computer, equipped to receive digitized or analog data from sensor interface 7. Controller 8 executes algorithms for analyzing sensed signals for detecting SRDB patterns. In an automatic CPAP system, controller 8 provides output to positive airway pressure (PAP) source 3 which generates positive pressure in response to sensed signal information that indicates apnea or hypopnea is imminent or occurring.

Sensors 5 for monitoring respiration are known for use with a patient mask and may include thermisters, a Doppler flowmeter, a micro-electromechanical system (or sensor) unit capable of detecting airflow by movement of miniature vanes, an accelerometer, or a pressure transducer. Examples of methods and apparatus for sensing air flow associated with respiration are generally described in the above-cited U.S. Pat. No. 5,551,419 and U.S. Pat. No. 5,645,053.

The system 1A further includes an implantable medical device (IMD) 10 capable of delivering a therapy to prevent or terminate sleep-related disordered breathing. In a preferred embodiment, IMD 10 is capable of delivering an electrical stimulation therapy to excitable body tissue in a way that prevents, terminates or reduces the duration or occurrence of SRDB. Accordingly, IMD 10 is coupled to at least one implantable medical lead 15 carrying one or more electrodes 22 for stimulating excitable tissue. IMD 10 is provided with a hermetically sealed, biocompatible housing 13 joined to a connecter block 12 provided for receiving one or more medical leads and achieving electrical coupling between IMD 10 and the conductor(s) carried by the lead 15 to electrode 22.

In a preferred embodiment, IMD 10 provides cardiac pacing therapy and is used for delivering overdrive pacing to the heart to prevent or reduce apnea episodes. Thus IMD 10 may be a single chamber, dual chamber, or multi-chamber cardiac pacemaker or implantable cardioverter defibrillator (ICD) coupled to one or more cardiac leads, which may be unipolar, bipolar or multipolar leads.

In another embodiment, IMD 10 is a biventricular or multichamber cardiac pacemaker capable of delivering ventricular resynchronization therapy for treating heart failure and thereby reducing the occurrence of nocturnal Cheyne-Stokes breathing. Cardiac resynchronization is emerging as an effective treatment for heart failure. See, for example, Ukkonen H, et al., Circulation 2003;107:28–31 and Kumar et al., Am J Geriatr Cardiol 2003;12:41–8. If a SRDB is recognized and nocturnal Cheyne-Stokes breathing, resynchronization therapy may be indicated. Cardiac pacing systems that may be used ventricular resynchronization are generally disclosed in U.S. Pat. No. 6,070,101 issued to Struble et al., and U.S. Pat. No. 6,480,742 issued to Stahmann et al., both patents incorporated herein by reference in their entirety.

External system 2A is preferably used to collect respiration data to allow patient screening and diagnosis of SRDB. External system 2A is further used to monitor respiration for detecting SRDB and storing data related to SRDB such that SRDB detection and metrics are available for optimizing and/or controlling the delivery of a therapy from IMD 10. Thus, IMD 10 is preferably in communication with external system 2A via a telemetry link 48 between controller 8 and IMD 10. As such, controller 8 is equipped with a communications unit 9 for sending and receiving information to and from IMD 10. Numerous types of telemetric communication systems, which are known for use with implantable medical devices, may be used with the present invention.

FIG. 1B is a schematic diagram of an alternative embodiment of a system, generally labeled as 1b, provided by the present invention for monitoring for sleep-related disordered breathing (SRDB) and delivering a therapeutic intervention. In system 1b, the external monitoring system 2b, includes a controller 8 and patient mask 6 as described above, however, in this embodiment external system 2b is provided for monitoring respiration without CPAP delivery capabilities. Hence, external system 1b does not include a positive pressure source. Sensor interface 7 receives input from sensors 5 along signal line 19. Signal line 19 may be provided as a cable connected between sensors 5 and interface 7 but is preferably provided as a telemetric or radio-frequency communication link such that no physical connection between mask 6 and interface 7 is needed. By removing the positive pressure source from external system 2b, an air hose connected to patient mask 6 is also unnecessary. Removal of the air hose makes mask 6 less cumbersome for the patient to wear during sleep. Replacement of sensor cables by radio-frequency or other telemetric communication between sensors 5 and interface 7 further reduces the inconvenience of wearing mask 6 during sleep. Thus, external system 2b is expected to be more readily accepted by a patient than external systems that require a breathing mask to be tethered to an air hose or other cables. Greater patient compliance in wearing the mask on a regular nightly basis will result in improved therapy delivery and greater patient benefit.

Figure 2:
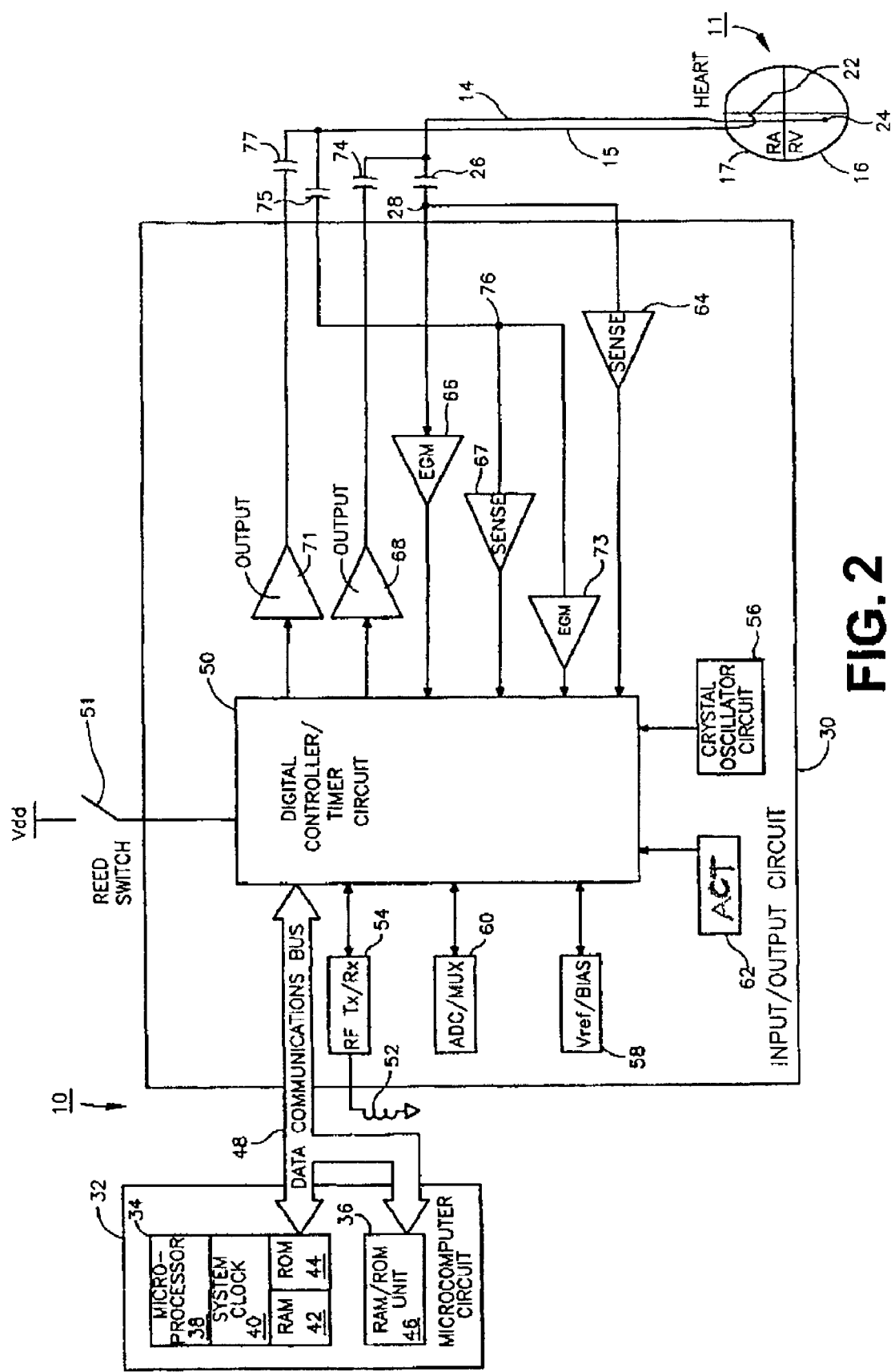
FIG. 2 is a functional block diagram of an exemplary implantable medical device that may be included in the systems of FIG. 1A or 1B for delivering overdrive cardiac pacing for alleviating sleep disordered breathing.

FIG. 2 is a functional block diagram of an exemplary implantable medical device for delivering overdrive cardiac pacing for alleviating sleep disordered breathing. Device 10 is coupled to the heart 11 by way of at least one cardiac lead for sensing an EGM signal and delivering cardiac pacing as needed. Lead 14 includes an endocardial electrode 24 located near its distal end and positioned within the right ventricle 16. Electrode 24 is electrically coupled by a conductor insulated within lead 14 to device 10 through an input capacitor 26 to a terminal 28. A second lead 15 includes a distally located endocardial electrode 22 positioned within the right atrium 17. Electrode 22 is electrically coupled by a conductor insulated within lead 15 to device 10 through an input capacitor 75 to a terminal 76. It is recognized that alternative lead and electrode systems may be used. For example, for the purposes of the present invention, dual chamber sensing is not required, and detection of a heart rate may be performed from sensing EGM signals in the atrium.

Input/output circuit 30 contains the operating input and output analog circuits for digital controlling and timing circuits needed for the detection of the intrinsic heart rhythm, and for the application of pacing pulses to the heart to control its rate under the control of software-implemented algorithms in a microcontroller 32. Cardiac signals sensed by the atrial electrode 22 are available as input to atrial sense amplifier 67 for the detection of atrial depolarizations, known as "P-waves". Cardiac signals sensed by the ventricular electrode 24 are available as input to ventricular sense amplifier 64 for the detection of ventricular depolarizations, known as "R-waves." Atrial sense amplifier 67 and ventricular sense amplifier 64 are preferably automatic gain controlled amplifiers with adjustable sensing thresholds. The general operation of the sense amplifiers 64 and 67 may correspond to that disclosed in U.S. Pat. No. 5,117,824, by Keimel, et al., incorporated herein by reference in its entirety. Whenever a signal received by the ventricular sense amplifier 64 exceeds a ventricular sensing threshold, an R-out signal is generated as output from sense amplifier 64 and received as input to digital controller and timer circuit 50. Likewise, whenever a signal received by atrial sense amplifier 67 exceeds an atrial sensing threshold, a P-out signal is generated as output from sense amplifier 67 and received as input to digital controller and timer circuit 50. P-out and R-out signals reset escape intervals, which are used to control the timing of pacing pulse delivery and are set by digital controller and timer circuit 50.

Microcontroller 32 includes an on-board circuit 34 and an off-board circuit 36. On-board circuit 34 includes a microprocessor 38, a system clock 40, and onboard RAM 42 and ROM 44. Off-board circuit 36 includes a RAM/ROM unit 46. Microcontroller 32 is coupled to digital controller and timer circuit 50 via a data communications bus 48. Microcontroller 32 may be fabricated from custom IC devices augmented by standard RAM/ROM components.

An antenna 52 is connected to input/output circuit 30 for purposes of uplink/downlink telemetry through a radio frequency (RF) transmitter/receiver 54. Telemetering both analog and digital data between antenna 52 and an external device, such as an external programmer (not shown), may be accomplished using numerous types of telemetry systems known in the art for use in implantable devices. Antenna 52 may also be used to receive telemetered signals from a patient activator that allows the patient to trigger certain device functions. In one embodiment of the present invention, disordered breathing monitoring may be triggered by the patient using a patient activator when he/she desires monitoring to commence, such as when going to bed at night. Patient activation devices are known in the art of cardiac rhythm management. Various mechanisms for patient-triggering of an implantable device function are generally described in U.S. Pat. No. 5,987,352, issued to Klein et al., incorporated herein by reference in its entirety.

A crystal oscillator circuit 56, typically a 32,768 Hz crystal-controlled oscillator, provides main timing clock signals to digital controller and timer circuit 50. A Vref/Bias circuit 58 generates a stable voltage reference and bias currents for the analog circuits of input/output circuit 30. An A/D converter and multiplexer circuit (ADC/MUX) 60 digitizes analog signals and voltages for uplinking and downlinking by telemetry, and for use by digital controller and timer circuit 50 and algorithms executed by microcontroller 32 during various device functions.

Operating commands for controlling the timing of the pacemaker are coupled by bus 48 to digital controller and timer circuit 50 wherein digital timers set escape intervals used for controlling the timing of pacing pulse delivery, as well as various refractory, blanking, and other timing windows for controlling the operation of the peripheral components within input/output circuit 30.

Digital controller and timer circuit 50 is further coupled to electrogram (EGM) amplifiers 66 and 73 for receiving electrogram signals, which may be transmitted by uplink telemetry to an external device. Electrogram signals are also available for further waveform processing by microcontroller 32.

Output pulse generators 68 and 71 provide pacing stimuli to the patient's heart 11 through output capacitors 74 and 77 and leads 14 and 15 in response to pace trigger signals received from digital controller and timer circuit 50 each time an escape interval times out or in response to other stored commands. Device 10 may be capable of various operating modes known in the art such as DDD, DDI, WI, VOO, AOO, VDD, DVI, AAI, ADI, AAT and WT, and the like. Device 10 may further be capable of delivering pacing pulses in a rate-responsive mode such as DDDR, DDIR, AAIR, ADIR, VVIR, VOOR and VVTR, and the like.

In response to the detection of a disordered breathing pattern, pacing pulses may be applied to the heart at a higher than normal rate, e.g. 90 bpm. A device for treating sleep apnea by stimulating the heart at a higher rate than the heart's natural rate is generally disclosed in the above-cited U.S. Pat. No. 6,126,611 issued to Bourgeois et al.

Device 10 may further include an activity sensor 62. An activity sensor may be incorporated as a piezoelectric element sensitive to body movements such that a signal from the activity sensor is correlated to the level of a patient's activity. The use of activity sensors is known in the art of rate-responsive pacemakers. An activity sensor may be implemented, for example, as generally disclosed in commonly assigned U.S. Pat. No. 5,052,388, issued to Sivula et al., incorporated herein by reference in its entirety.

In accordance with one embodiment of the present invention, the activity sensor 62 may be used in detecting a sleep state. Methods for detecting when a patient is likely to be asleep are known for use in cardiac rhythm management devices. Such methods may be based on one or more sensor inputs in conjunction with a real-time clock. Sensor signals that may be used for detecting a sleeping state may include an activity sensor, a respiration sensor, a posture sensor, a blood temperature sensor, etc. An implantable multi-axis position and activity sensor is disclosed in U.S. Pat. No. 5,233,984, issued to Thompson, incorporated herein by reference in its entirety. A device capable of determining when a patient is likely to be asleep is disclosed in U.S. Pat. No. 5,630,834, issued to Bardy and U.S. Pat. No. 5,814,087 issued to Renirie, both incorporated herein by reference in its entirety.

Figure 3:
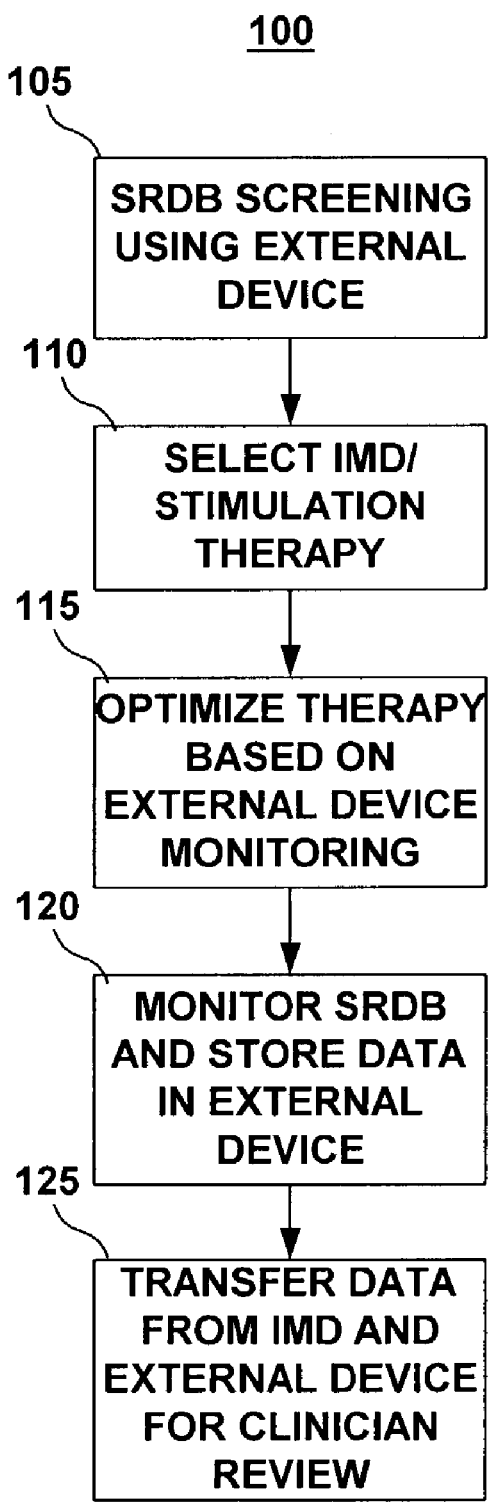
FIG. 3 is a flow chart providing an overview of a general method for using the system of FIG. 1A or 1B.

FIG. 3 is a flow chart providing an overview of a general method for using the system of FIG. 1A or 1B. Patients may be screened for sleep-related breathing disorders (SRBD) using the external system at step 105. The external system may be delivered to a patient's home for overnight use in lieu of performing a polysomonographic study in a clinic. The external system performs sleep monitoring by sensing respiratory-related signals and storing information indicating the occurrence of apnea/hypopnea events. When the external system is provided as an automatic CPAP system, positive airway pressure may be delivered automatically when apnea or hypopnea is detected. By providing an external system for home use, costly and inconvenient clinical studies may be eliminated or designated only for patients who need additional study. Thus, the external system for home screening will allow a larger number of patients to be screened for SRDB and thereby reduce the number of undiagnosed cases of SRDB.

Based on diagnostic information provided by the external system used for home screening, a clinician may diagnose a patient with a SRDB. Based on this diagnosis, the physician may select an implantable medical device at step 110 for treating the SRDB condition. The IMD selected will depend on the diagnosis made. For example, a patient determined to experience nocturnal Cheyne-Stokes breathing may be diagnosed with heart failure. A biventricular or multichamber cardiac pacing device may be prescribed to provide cardiac resynchronization therapy to alleviate the heart failure condition.

If a patient is diagnosed with sleep apnea, a clinician may prescribe a dual chamber pacemaker, such as device 10 of FIG. 2, capable of providing nocturnal atrial overdrive pacing to reduce the occurrence of sleep apnea. Alternatively, other types of implantable electrical stimulation devices may be selected for stimulating the vagus nerve, the central nervous system, muscles of the upper airway, the diaphragm, or any other electrical stimulation therapy for alleviating SRDB.

At step 115, the IMD operation is optimized for treating the diagnosed SRDB condition based on data collected by the external system. The external system may provide respiration-related data directly to the IMD. Data could be downlinked on a breath-by-breath basis, upon updating SRDB trended data, or upon updating data for an entire sleeping period or another periodic basis such as weekly. Downlinked data is then used by the IMD to adjust electrical stimulation parameters to improve the effectiveness of the therapy. Alternatively, the external system may analyze respiration-related data and determine an appropriate therapy adjustment to be made. In this embodiment, a therapy adjustment command is downlinked from the external device to the IMD.

At step 120, the external system continues to monitor for SRDB and may store respiration-related or disordered breathing episode data. Continued monitoring of SRDB allows optimal therapy delivery parameters to be maintained under changing patient conditions, such as weight loss or gain, and allows a physician to monitor patient compliance. Data that may be of interest to a physician may include number of SRDB episodes, apnea length, hyperpnea length, periodic breathing cycle time, apnea-hypopnea index, or other parameters. Determination and storage of metrics of respiratory disturbances is generally described in pending non-provisional U.S. patent application Ser. No. 10/419,467 by Yong et al. filed on even date herewith and entitled, "METHOD AND APPARATUS FOR DETECTING RESPIRATORY DISTURBANCES," said application is hereby incorporated by reference herein. Said application was based upon provisional U.S. patent application serial No. 60/439,303 filed 10 Jan. 2003.

At step 125, stored data from the external system and the IMD are preferably available for transfer to a clinical center for review by a clinician. Data is preferably transferable to an internet-compatible central patient management network for remote monitoring. A bi-directional communication system that is network, Internet, intranet and worldwide web compatible to enable chronic monitoring based on data obtained from implantable monitors is generally disclosed in International Publication No. WO 01/70103 A2, issued to Webb et al, incorporated herein by reference in its entirety.

In a preferred embodiment, the IMD selected for treating sleep apnea is a cardiac pacemaker, such as the pacemaker shown in FIG. 2, or an implantable cardioverter defibrillator (ICD) that includes cardiac pacing capabilities. Nocturnal overdrive pacing is the preferred sleep apnea therapy employed in the present invention because it is expected to be as effective as CPAP therapy at reducing the apnea-hypopnea index, is not fully dependent on patient compliance, and is not expected to arouse the patient causing sleep fragmentation.

Figure 4:
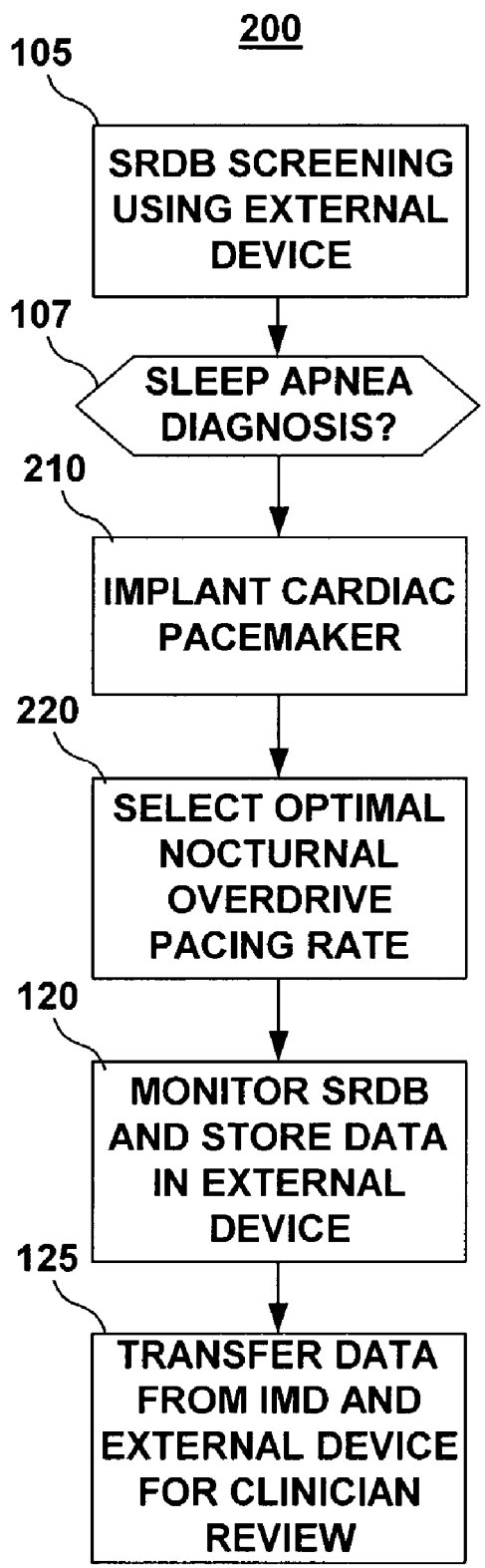
FIG. 4 is a flow chart summarizing the steps included in a method for monitoring and treating sleep apnea in accordance with one embodiment of the present invention wherein the monitoring and therapy delivery system of FIG. 1A or 1B employs an implantable cardiac pacemaker.

FIG. 4 is a flow chart summarizing the steps included in a method for monitoring and treating sleep apnea in accordance with one embodiment of the present invention wherein the monitoring and therapy delivery system employs an implantable cardiac pacemaker. Identically numbered steps in FIG. 4 correspond to those in FIG. 3. Initial screening for SRDB is performed at step 105 using the external system as described above. If sleep apnea is diagnosed by a clinician based on screening data at step 107, a cardiac pacemaker is implanted at step 210 for treating the sleep apnea. Accordingly, the pacemaker is capable of delivering a different base pacing rate at night than during the day. Night overdrive pacing may be enabled at a pre-set time of day, by a trigger signal received from the external system or by other sleep detection methods known in the art of cardiac pacing.

At step 220, the optimal nocturnal atrial overdrive pacing (NOP) rate is selected. The optimal rate is selected based on testing different NOP rates and monitoring the incidence of SRDB. Test NOP rates may be applied on different nights or during a single night for a given interval of time. A test protocol is preferably delivered automatically by the IMD, and the applied test rate transmitted to the external monitoring system. Alternatively, delivery of a test protocol may be controlled by the external system in communication with the IMD. The external system may downlink a test rate to be tested to the IMD. During NOP any given test rate, respiration is monitored by the external system to determined if the applied NOP rate is effective. SRDB is detected and the frequency of apnea detections or other SRDB metrics are determined and stored by the external device with the corresponding NOP rate.

The physician may review data stored by the external system and manually select the NOP rate that results in the lowest incidence of apnea episodes, lowest apnea/hypopnea index, or other SRDB metric. Alternatively, the system may automatically identify the most effective NOP rate based on improved SRDB metrics and set the NOP rate accordingly.

At steps 120 and 125, continued monitoring of SRDB and data transfer may be performed as described in conjunction with FIG. 3. One advantage of providing NOP is that once an optimal NOP rate is selected and programmed, a patient that becomes non-compliant with continued usage of the mask for monitoring SRDB can still benefit from NOP.

Figure 5:
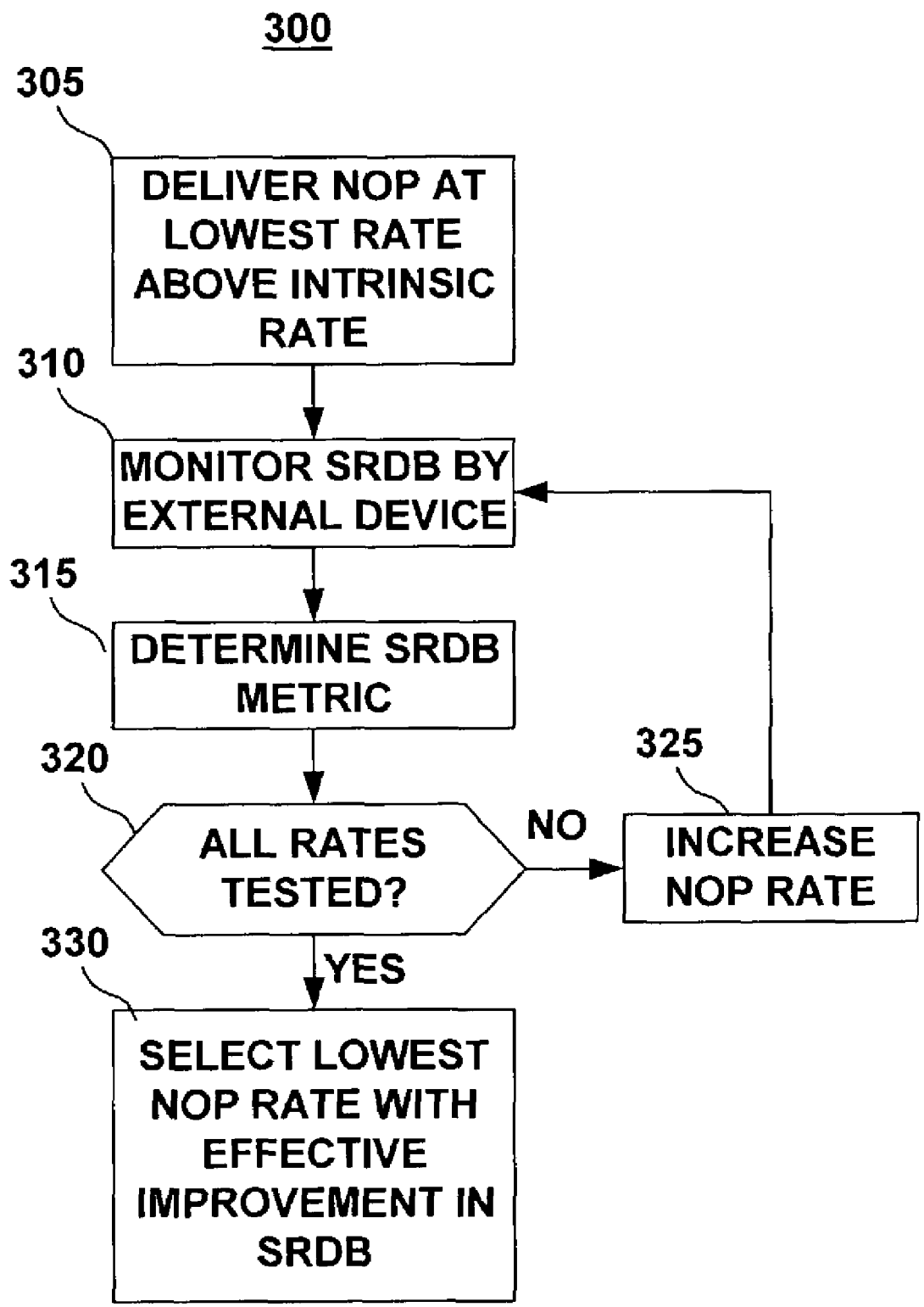
FIG. 5 is a flow chart summarizing steps included in one method for automatically determining and setting an optimal nocturnal overdrive pacing rate in response to respiratory data received from the external monitoring system included in the system of FIG. 1A or 1B.

FIG. 5 is a flow chart summarizing steps included in one method for automatically determining and setting an optimal nocturnal overdrive pacing rate in response to respiratory data received from the external system. In method 300, a number of NOP rates are automatically tested and evaluated to determine the lowest effective rate. Generally, it is preferable to pace the heart at the lowest rate that effectively improves SRDB in order to conserve pacemaker battery energy and avoid undue overdrive pacing which may be poorly tolerated by a failing heart.

At step 301, a baseline SRDB metric(s) is determined prior to delivering any therapeutic intervention. At step 305, the IMD delivers NOP at a rate just above the sensed intrinsic heart rate, for example 5 to 10 bpm greater than the intrinsic heart rate. If the intrinsic heart rate is not sensed, for example due to an intrinsic rate less than the programmed base pacing rate, a nominal NOP rate may be selected. At step 310, the external device monitors for SRDB and determines a SRDB metric at step 315 for the current NOP rate. In one embodiment, the current pacing rate is uplinked to the external device and the associated SRDB metric and current pacing rate are stored by the external device. In an alternative embodiment, the SRDB metric is downlinked to the IMD and stored with the current pacing rate in the memory of the IMD.

At least two NOP rates are tested and compared to determine the most effective rate. Preferably, multiple NOP rates, for example rates at intervals of 5 to 10 bpm, may be tested and compared to determine the most effective rate. The NOP rate is adjusted at step 325 to the next test rate, and the corresponding SRDB metric is determined and stored at step 315 until all test rates have been evaluated. Once all test rates have been applied, as determined at step 320, the lowest rate having an effective improvement in SRDB is selected as the NOP rate at step 330. An effective improvement in SRDB may be predefined as any decrease in the metric(s) used to evaluate SRDB, such as decreased AHI. Alternatively, an effective improvement may be gauged as a required amount of decrease in the metric. For example, an effective decrease may be defined as a decrease of at least 5 apnea/hypopnea events per hour. If more than one NOP rate successfully improves SRDB by the required amount, the lowest, effective NOP rate is selected. If no NOP rates meet the desired SRDB improvement, the lowest rate that showed any improvement may be selected.

If the external monitoring system has stored the test rates and corresponding SRDB metrics, the external system may identify the lowest effective rate and uplink that information to the IMD. The IMD then sets the NOP rate accordingly. If the IMD has stored the test rates and corresponding SRDB metrics, then the IMD automatically programs the NOP rate based on this information and may optionally uplink the selected rate and supporting data to the external device for logging purposes. Once the optimal rate is selected, NOP is delivered at the selected rate until a re-optimization of NOP rate is performed. A re-evaluation of the lowest, effective rate may be performed according to method 300, as just described, on a periodic, automatic basis, upon a manual command delivered by a clinician or the patient using the external system, or upon an automatic trigger signal from the external device when the external device detects a worsening of SRDB based on continued monitoring.

If the patient remains compliant with the use of the mask, continued monitoring of SRDB by the external system advantageously allows closed-loop feedback of respiration parameters to the IMD so that the nocturnal overdrive pacing rate may be re-optimized if a worsening of SRDB occurs.

Figure 6:
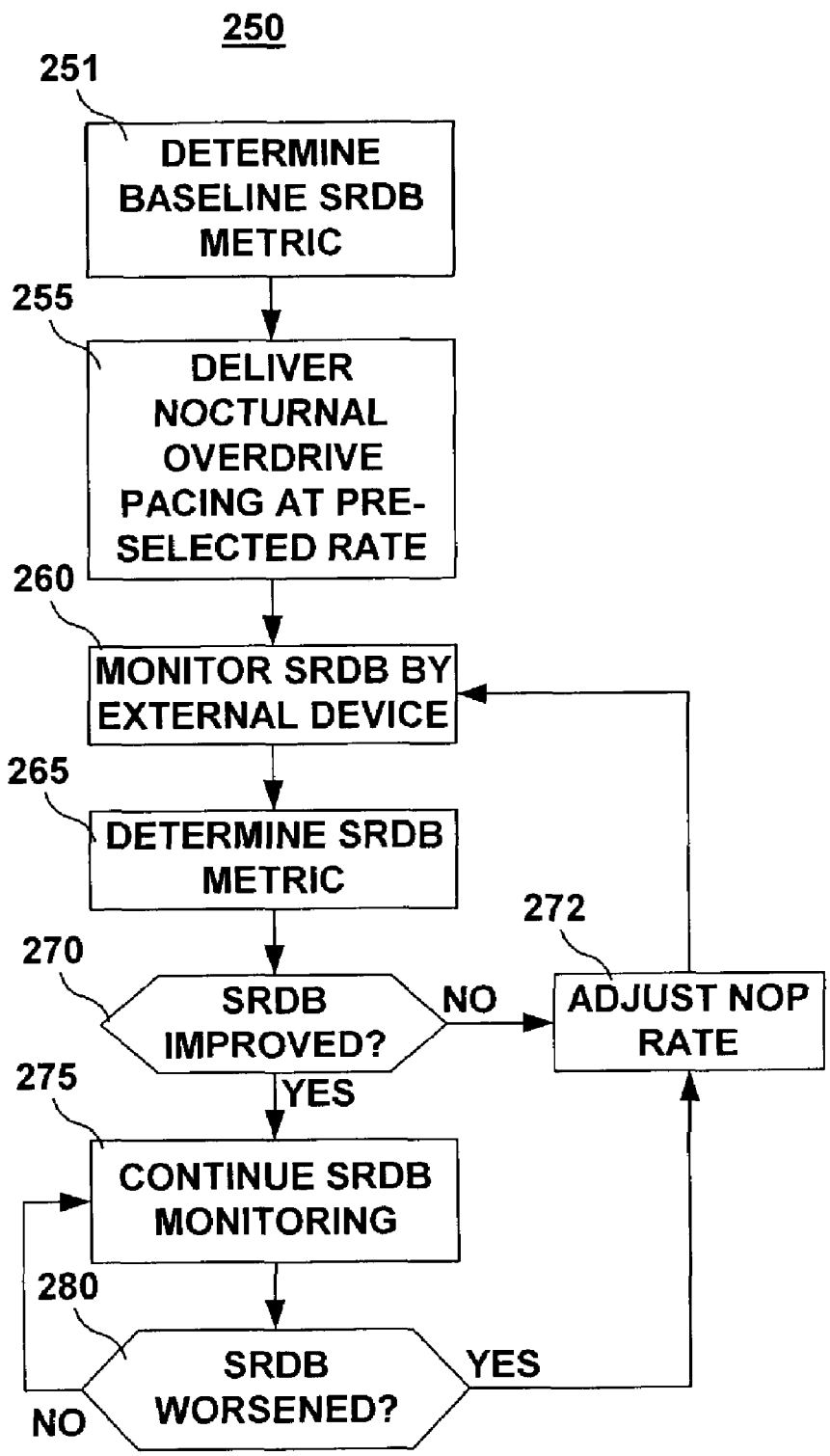
FIG. 6 is a flow chart summarizing steps included in a method for automatically adjusting the nocturnal overdrive pacing rate in the implantable cardiac pacemaker in response to respiratory data received from the external monitoring system.

FIG. 6 is a flow chart summarizing steps included in a method for automatically adjusting the nocturnal overdrive pacing rate in the implantable cardiac pacemaker in response to respiratory data received from the external system. A baseline metric(s) of the SRBD is obtained at step 251. This baseline measure may be obtained during the initial screening for SRDB and is preferably the patient's apnea-hypopnea index, but could alternatively or additionally include a measure of apnea, hypopnea or hyperpnea length, periodic breathing cycle length or other metrics of SRDB determined prior to delivering any therapeutic intervention.

At step 255, nocturnal overdrive pacing (NOP) is initially delivered at a nominal rate or other pre-selected rate, such as an optimal rate determined using methods described above. A nominal rate may be a fixed rate, for example 80 to 90 beats per minute, or may be a given interval greater than the intrinsically sensed heart rate, for example 10 to 20 beats per minute greater than the intrinsic heart rate.

At step 260, respiration is monitored by the external system for detecting episodes of SRDB. At step 265, the SRDB metric is re-determined after a predetermined monitoring period at the pre-selected NOP rate. NOP is preferably applied for at least one hour before re-determining the SRDB and may be applied for an entire night after which nighttime summary data is obtained. If the metric(s) of SRDB show improvement, for example a reduction in apnea/hypopnea index, then NOP is continued at the nominal rate with continued monitoring of SRDB by the external device at step 275. If improvement in SRDB metric(s) is not found at the pre-selected NOP rate at step 270, or if an improved SRDB metric worsens later during continued monitoring as determined at decision step 280, the NOP rate is adjusted at step 272. A higher NOP rate may be required to effectively reduce the incidence of apnea or hypopnea.

Closed-loop feedback is accomplished by transferring data relating to the SRDB metric(s) from the external monitoring system to the IMD. Adjustment of the NOP rate is made by the IMD based on this data. Thus if the SRDB metric(s) are improved and stable, no adjustment to the NOP rate is made. If no improvement or a worsening in SRDB metric(s) is indicated, the IMD automatically increases the NOP rate up to a predetermined maximum rate. Data may be transferred to the IMD upon each re-determination of a SRDB metric. A re-determination may be performed after a specified period of time, on a breath-by-breath basis, or after an entire sleeping period. In one embodiment, respiration data may be transferred to the IMD and determination of a worsening or improvement of SRDB is performed by the IMD. In another embodiment, the external monitoring system determines if a lack of improvement or worsening of SRDB has occurred and transfers information to the IMD to trigger an NOP rate adjustment.

After adjusting the NOP rate at step 272, the external monitoring system returns to step 260 to continue monitoring respiration. After a given period of time the SRDB metric(s) is redetermined at step 265. The SRDB metric is evaluated at step 270 to determine whether the adjusted NOP rate has been effective. Re-optimization of NOP rate is thus accomplished by continuous monitoring by the external device and adjustments of the NOP by the IMD whenever a worsening of SRDB is detected.

Figure 7:
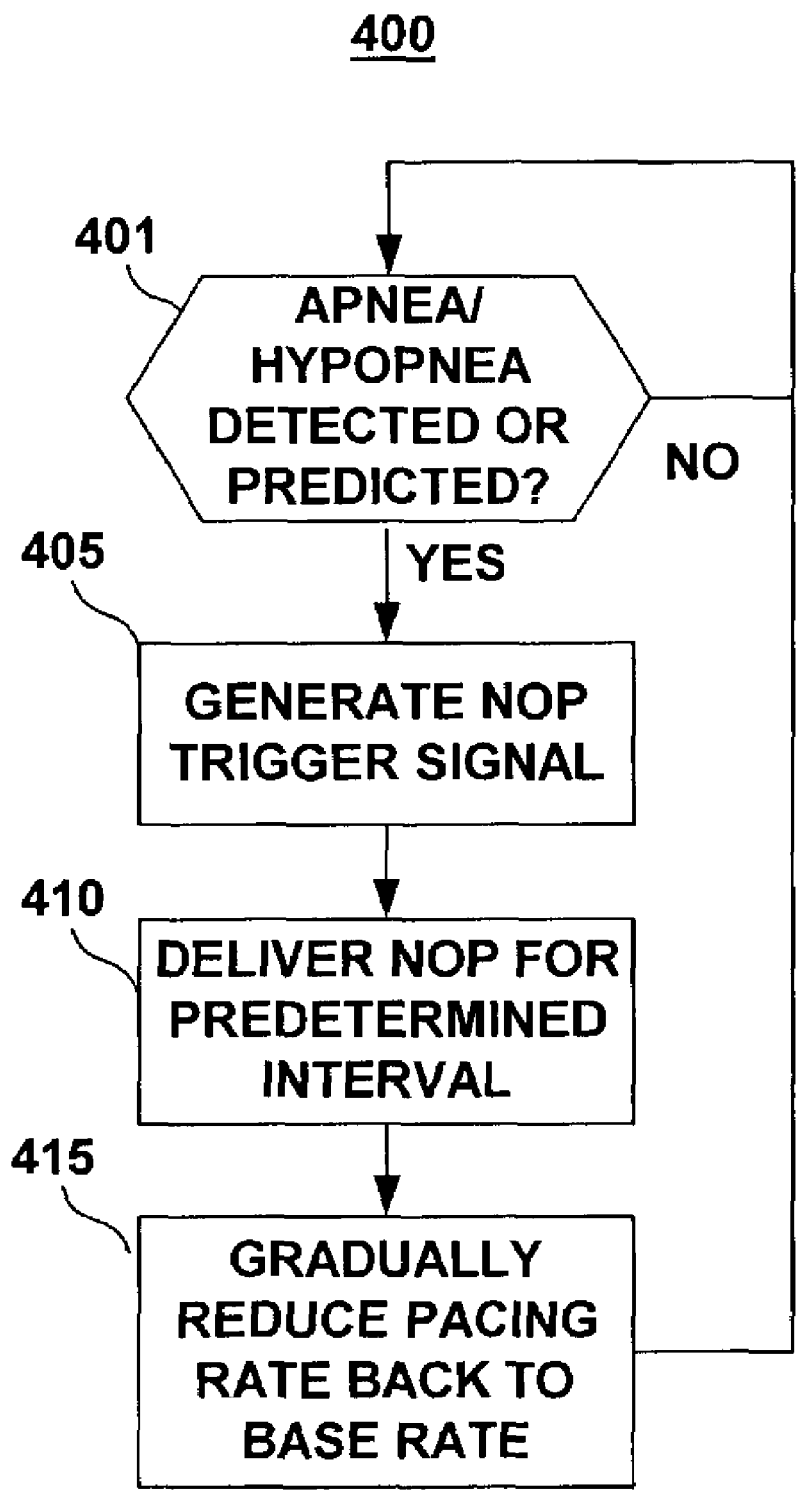
FIG. 7 is a flow chart summarizing steps included in a method for delivering SRDB therapy in an episode-based mode using an implantable medical device in accordance with the present invention.

FIG. 7 is a flow chart summarizing steps included in a method for delivering SRDB therapy in an episode-based mode using an IMD in accordance with the present invention. NOP may be delivered continuously through the night to prevent or reduce the frequency of apnea/hypopnea episodes. Alternatively the delivery of NOP or any other selected therapy may be delivered on an "as-needed basis," triggered by the detection of an apnea/hypopnea episode or the prediction of an imminent apnea/hypopnea event.

Method 400 of FIG. 7 allows therapy to be delivered in an episode-based mode. At decision step 401, method 400 waits for an apnea/hypopnea detection or prediction to be made based on the SRDB monitoring performed by the external monitoring system. Once a detection or prediction is made, the external system generates a NOP trigger signal at step 405 that is downlinked to the IMD to initiate NOP. NOP is delivered by the IMD at step 410 for a predetermined period of time. In one embodiment, NOP is delivered for a fixed interval of time, on the order of 10 to 15 minutes, to end the apnea/hypopnea episode, preferably without arousal, and with the intent of preventing a subsequent apnea/hypopnea episode. If additional apnea/hypopnea episodes are detected, the triggered NOP interval may be lengthened on subsequently detected episodes. In an alternative embodiment, after being triggered once, NOP is delivered for the remainder of the sleeping period. In this embodiment, NOP is started only when it is needed for preventing or terminating an apnea/hypopnea episode then remains on until the patient is expected to be awake such that apnea/hypopnea episodes are reduced or eliminated throughout the remainder of the patient's sleep. At step 415, the pacing rate is gradually reduced from the higher NOP rate to the lower, programmed base rate at the end of the NOP interval.

The methods described in conjunction with FIGS. 5A, 5B and 6 relate to nocturnal overdrive pacing as a therapy for SRDB delivered by an implantable device. It is recognized, however, that other types of therapies delivered by an IMD may be adjusted, optimized or triggered based on feedback received from respiration monitoring performed by the external monitoring system. For example, electrical pulse energy, stimulation rate or timing, pulse shape, pulse train frequency, pulse number, or other operational parameters used by an implantable medical device for delivering electrical stimulation therapy for treating SRDB may be adjusted based on feedback received from and external monitoring system. Likewise, prediction or detection of an apnea/hypopnea episode may be used to trigger therapies other than NOP. As indicated previously, other types of electrical stimulation therapies that may be delivered by an IMD for treating SRDB may include stimulation of the vagus nerve, upper airway muscles, hypoglossal nerve, diaphragm, or other neuromuscular or central nervous system stimulation or cardiac resynchronization.

While the above discussion of the illustrated embodiments, primarily focused on detection of disordered breathing via an external apparatus with therapy provided via an implantable medical apparatus, for appropriately featured apparatuses the opposite modality may be implemented. In this case, a detection signal of a disordered breathing event by an implantable medical apparatus, such as an implanted pulse generator having sensor capabilities, is provided to an external disordered breathing therapy apparatus, such as a CPAP machine. Upon receipt of the detection signal, the operating pressure of said CPAP machine may be suitably titrated (e.g., increasing positive airway pressure) until such time as the disordered breathing event terminates. Upon termination of the event, the implantable pulse generator preferably provides an "event terminated" signal to the external apparatus which then reverts to a different, preferably less aggressive therapy modality. Of course, at least for CPAP therapy, the changes in CPAP pressure may be gradual- or step-changes, or a combination of both types of changes. Also, in addition to changing the CPAP airway pressure settings, so-called nocturnal overdrive pacing (NOP) may be initiated so that the patient's heart rate is elevated. As disclosed in U.S. Pat. No. 6,126,611 to Bourgeois et al. such NOP can provide relief from sleep apnea (or certain forms of sleep disordered breathing).

While detailed descriptions of preferred embodiments have been provided herein, it is recognized that numerous variations are possible. The embodiments described should be considered exemplary, and not limiting, with regard to the following claims.

What is claimed is:

1. A system for monitoring and treating sleep-related disordered breathing, comprising:
   an external monitoring system further comprising:
      a patient mask equipped with at least one sensor means for generating an output signal relating to a patient's respiration; and
      a controller for receiving the output signal and detecting a disordered breathing event, and
   an implantable medical device means for delivering an electrical stimulation therapy and for reducing a number of episodes of sleep-related disordered breathing wherein said implantable medical device further comprises means for sending, receiving, and processing data from the external monitoring system, and wherein said data comprises information related to respiration of the patient.

2. A system according to claim 1, the external monitoring system further includes a positive airway pressure source for generating positive pressure for maintaining airway patency.

3. A method for monitoring and treating sleep-related disordered breathing comprising:
   monitoring a patient's respiration to detect sleep-related disordered breathing using an external monitoring devices having at least one external sensor, the external monitoring devices coupled with a continuous positive airway pressure (CPAC) device, wherein said at least one sensor measures an aspect of respiration of the patient;
   storing a diagnostic data related to at least one detected sleep-related disordered breathing episode for analysis in the external monitoring device;
   delivering an electrical stimulation therapy from an implantable medical device to excitable cardiac tissue to reduce the incidence of the sleep-related disordered breathing;
   transferring the diagnostic data from the external monitoring device to the implantable medical device; and
   optimizing delivery of the electrical cardiac stimulation therapy based on the diagnostic data.

4. A hybrid apparatus for detecting sleep disordered breathing episode(s) and providing a therapy to reduce said episode(s) comprising an implantable medical device apparatus telemetrically coupled to an external continuous positive airway pressure (CPAC) apparatus, and comprising:
   means for detecting a sleep disordered breathing event with the external CPAP apparatus and providing a detection signal;
   means for communicating said detection signal to the implantable medical device; and
   means for providing a cardiac electrical stimulation therapy for terminating said sleep disordered breathing event with the implantable medical device.

5. A hybrid apparatus according to claim 4, wherein the cardiac electrical stimulation is an elevated cardiac pacing rate.

6. A hybrid apparatus according to claim 4, wherein said implantable medical device comprises at least one sensor for sensing a cyclical variation of a physiologic parameter of a patient, wherein said cyclical variation relates to the sleep disordered breathing event.

7. A hybrid apparatus according to claim 6, wherein said at least one sensor comprises a one of the following: an impedance circuit for measuring minute ventilation of the patient, a heart rate sensor, a blood oximetry sensor, or an electrogram (EGM) circuit means.

8. A hybrid apparatus according to claim 4, wherein said means for communicating comprises a local telemetry technique that provides communication only in the event that the detection signal indicative of a sleep disordered breathing event is provided.

9. A hybrid apparatus according to claim 4, further comprising a means for providing an event terminated signal from the external CPAP apparatus to said implantable medical device upon termination of said sleep disordered breathing episode.

10. A hybrid apparatus according to claim 5, wherein a therapy provided by the CPAP apparatus is gradually increased in magnitude until said therapy reaches a preset maximum Threshold value or until termination of the sleep disordered breathing episode, wherein said termination is measured by either the CPAP machine or the implantable medical device.

11. A computer readable medium including instructions that when executed cause a computer to perform a method via a hybrid apparatus for detecting sleep disordered breathing and providing a sleep disordered breathing therapy, the hybrid apparatus including an implantable medical device telemetrically coupled to an external continuous positive airway pressure (CPAC) apparatus, comprising:
   instructions for detecting a sleep disordered breathing event with the implantable medical device and providing a detection signal;

instructions for communicating said detection signal to the CPAP apparatus;

instructions for providing a cardiac electrical stimulation therapy for terminating said sleep disordered breathing event.

12. A computer readable medium including instructions that when executed cause a computer to perform a method for detecting sleep disordered breathing episode(s) and providing a therapy to reduce said episode(s) via a system including an implantable medical device telemetrically coupled to an external continuous positive airway pressure (CPAC) apparatus, comprising:

instructions for detecting a sleep disordered breathing event with the implantable medical device and providing a detection signal;

instructions for communicating said detection signal to a non-implantable medical apparatus; and instructions for providing a combined therapy for terminating said sleep disordered breathing event from both the implantable medical device and the non-implantable medical apparatus.

* * * * *

UNITED STATES PATENT AND TRADEMARK OFFICE
CERTIFICATE OF CORRECTION

PATENT NO. : 7,025,730 B2
APPLICATION NO. : 10/419465
DATED : April 11, 2006
INVENTOR(S) : Cho et al.

It is certified that error appears in the above-identified patent and that said Letters Patent is hereby corrected as shown below:

Col. 13, line 59, please delete "claim 1, the external" and insert --claim 1, wherein the external--

Col. 14, line 19, delete "pressure (CPAC)" and insert --pressure (CPAP)--

Col. 14, line 64, delete "pressure (CPAC)" and insert --pressure (CPAP)--

Col. 15, line 12, delete "pressure (CPAC)" and insert --pressure (CPAP)--

Signed and Sealed this

Third Day of April, 2007

JON W. DUDAS
*Director of the United States Patent and Trademark Office*